United States Patent [19]

Ananthanarayanan

[11] Patent Number: 5,169,865
[45] Date of Patent: Dec. 8, 1992

[54] METHOD AND COMPOSITION FOR CALCIUM BINDING, TRANSLOCATION AND MEDIATING

[75] Inventor: V. S. Ananthanarayanan, Ancaster, Canada

[73] Assignee: Seabright Corporation Limited, Newfoundland, Canada

[21] Appl. No.: 323,421

[22] Filed: Mar. 14, 1989

[30] Foreign Application Priority Data

Jul. 25, 1988 [CA] Canada .................................... 572968

[51] Int. Cl.$^5$ ............................................ A01N 37/34
[52] U.S. Cl. .................................. 514/519; 424/450; 558/408
[58] Field of Search ................... 424/450; 514/519; 558/408

[56] References Cited

U.S. PATENT DOCUMENTS

| | | | |
|---|---|---|---|
| 4,235,871 | 4/1980 | Papahadjononlo | 424/450 |
| 4,348,387 | 9/1982 | Brownlee et al. | 514/4 |
| 4,392,996 | 7/1983 | Sternberger | 530/315 |
| 4,618,598 | 10/1986 | Cohn | 514/13 |
| 4,668,772 | 5/1987 | Lee | 530/300 |
| 4,680,283 | 7/1987 | Veber et al. | 514/18 |
| 4,725,462 | 2/1988 | Haynes | 424/450 |
| 4,731,210 | 3/1988 | Weder et al. | 424/450 |
| 4,885,172 | 12/1989 | Bally et al. | 424/450 |

FOREIGN PATENT DOCUMENTS

3339861 5/1985 Fed. Rep. of Germany .
3515335 10/1986 Fed. Rep. of Germany .

OTHER PUBLICATIONS

94: 202515y, "Org. Ca. Antagonist", Malaisse et al. (1981).
99:8220c, "Inhibition of Sodium Dependent Ca Uptake by Verapamil", Erdreich et al. (1983).
97:175060z, "Inhibition of Calcium Antagonists of Ionophore Mediated Calcium Transport in Liposomes", Deleers (1982).
96:136367, "Evidence that Stimulation of TRH and CA Mediated Mechanisms", Geras et al. (1982).
CA107:32936d, Erdreich et al., "Possible Involvement of Phospholipid Phase Membranes in Mediating Effect of Verapamil", (1987).
CA101:122776g, Erdreich et al., "Inhibition of Ca++ Uptake", (1984).
CA100:185733r, Hattori et al., "Influences of Ca++, Verapamil on Positive Inotropic Effects", (1984).
CA92:121616, Malaisse et al., "Protective Effect of Calcium Against Verapamil", (1980).
CA105:167045s, "Purified Dihydropyridine Binding Site", Flockerzi et al., (1986).
CA106:90196, "Pharm. Formulation Containing Dihydropyridines", Schlossmann et al., (1987).
CA103:166155z, "Parenteral Dihydropyridine Liposome Formulations", Schlossmann et al., (1985).

(List continued on next page.)

*Primary Examiner*—Lester L. Lee
*Assistant Examiner*—E. J. Kraus
*Attorney, Agent, or Firm*—Iver P. Cooper

[57] ABSTRACT

A method, and mediating agents are provided for mediating the physiological effects of hormones, neurotransmitters, calcium-channel antagonists, chemotactic peptides or chemotactic proteins. The mediating agents provided herein are bioactive conformations of peptide hormones, neurotransmitters, calcium-channel antagonist drugs or chemotatic peptides, or analogues, agonists or antagonists thereof, or synthetic analogue substances, having $Ca^{2+}$ and/or $Mg^{2+}$ ions optimally and optimally-conformationally bound to the respective compound. The $Ca^{2+}$ antagonist/agonist may bind $Mg^{2+}$ and thus may also block calcium-channel. In the one method, the concentration of intracellular $Ca^{2+}$ is raised by means of such mediating agents. A second method is also provided for delivering $Ca^{2+}$ and/or $Mg^{2+}$ to a membrane-bound receptor by transporting $Ca^{2+}$ and/or $Mg^{2+}$ through a cell membrane using the above-described mediating agents.

8 Claims, 3 Drawing Sheets

OTHER PUBLICATIONS

CA102:2255k, "Effect of Some 1,4 Dihydropyridine Deriv.", Panasenko et al., (1985).

"Lipsome Targeting in Vivo, Prob. & Opp.", Biol. Cell (1983) 47, 19–36.

Geras et al., Endocrinology 110; 901–906 (1982); Evidence that Stimulation of Thyrotropin and Prolactin Secretion by Thyrotropin-Releasing Hormone Occur via Different Calcium-Mediated Mechanisms . . . .

Erdreich and Rahamimoff; Biochem. Pharmacol. 36:1775–1780 (1987); The Possible Involvement of the Phospholipid Phase of Membranes in Mediating the Effects of Verapamil on $Ca^{2+}$ Transport.

Erdreich and Rahamimoff; Biochem. Pharmacol. 33:2315–2323 (1984); The Inhibition of Ca Uptake in Cardiac Membrane Vesicles by Verapamil.

Hattori and Kanno; Gen. Pharmac. 15:91–97 (1984); Influences of Extracellular Calcium Ions, Verapamil, and Calcium Antagonistic Cations on the Positive Inotropic Effects Mediated by . . . .

Malaisse; Experientia 35 1578–79 (1979); Protective Effect of Calcium Against the Verapamil-Induced Inhibition of Ionophore-Mediated Calcium Translocation.

Flockerzi et al.; Nature 323:66–68 (1986); Purified Dihydropyridine-Binding Site from Skeletal Muscle T-Tubules is a Functional Calcium Channel.

S (ppm)

FIG. 3.

METHOD AND COMPOSITION FOR CALCIUM BINDING, TRANSLOCATION AND MEDIATING

BACKGROUND OF THE INVENTION (a) Field of the Invention

This invention relates to a method and means for mediating the physiological effects of peptide hormones, neurotransmitters, drugs and chemotactic agents as well as the agonists, antagonists and synthetic analogues of these compounds. It also relates to the novel such mediating agents.

There are many hormones and neurotransmitters which have a physiological effect on the human body. The following are some examples:

Adrenocorticotropin hormone (ACTH) is a 24 amino acid-residue-long pituitary hormone which stimulates the secretion of adrenal cortical steroids and induces growth of the adrenal cortex.

Angiotensin is a hormone which acts on the adrenal gland to stimulate the release of aldosterone. It causes contraction of the smooth muscle. The amino acid sequence of horse angiotensin II is Asp-Arg-Val-Tyr-Ile-His-Pro-Phe.

Vasopressin and oxytocin belong to the neurophyseal family of peptide hormones. Both are 9-residue-long peptides containing a disulphide bridge and an amidated C-terminus.

```
Arg-Vasopressin:  Cys—Tyr—Phe—Gln—Asn—Cys—Pro—Arg—Gly—NH2
                  |___________________________|

Oxytocin:         Cys—Tyr—Ile—Gln—Asn—Cys—Pro—Leu—Gly—NH2
                  |___________________________|
```

Vasopresin has antidiurtetic and vasopressor effects while oxytocin induces contraction of smooth muscles, especially in the uterus and mammary glands.

Bombesin is a linear tetradecapetide hormone responsible for a wide range of biological activities. The latter include its action on the central nervous system as a stimulus to disrupt thermo-regulation causing the release of other hormones, e.g., insulin, glucagon, gastrin, prolactin and growth hormone and its stimulation of mitogenesis.

Bradykinin is a hormone belonging to a group of hypotensive peptides known as plasma kinins. It acts on smooth muscle, delicate peripheral vessels and increases capillary permeability. Its amino acid sequence is Arg-Pro-Pro-Gly-Phe-Ser-Pro-Phe-Arg.

β-casomorphin (Tyr-Pro-Phe-Pro-Gly-Pro-Ile) is a peptide hormone with opioid activity.

Cholecystokinin is a polypeptide hormone which causes gallbladder contraction. It stimulates the release of calcitonin and glucagon.

Met-enkaphalin and Leu-enkaphalin are pentapeptide hormones in the brain possessing opiate-like activity. The Met-enkaphalin shares a common precursor with ACTH and β-lipotropin. Its structure is:

Tyr-Gly-Gly-Phe-Met.

The endorphins are derived from β-lipoprotein and elicit reactions, e.g., analgesia, behavioral changes and growth hormone release.

Gastrins are heptadecapeptide hormones which are highly potent gastric secretion stimulants. The amino acid sequence of human gastrin I is 5-oxo-Pro-Gly-Pro-Trp-Leu-Glu-Glu-Ala-Tyr-Gly-Trp-Met-Asp-Phe-NH2.

Glucogen is a polypeptide hormone produced in the alpha cell of the islets of Langerhans in the pancreas, which appears to be present in increased concentrations in diabetes. Its amino acid sequence is His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Tyr-Leu-Met-Asn-Thr.

Insulin is a polypeptide hormone produced in the beta cells of the islets of Langerhans situated in the pancreas of all vertebrates. It is secreted directly into the bloodstream where it regulates carbohydrate metabolism, influences the synthesis of protein and of RNA, and the formation and storage of neutral lipids. The amino sequence of human insulin is LH is a gonodotrophic hormone which stimulates the synthesis of progesterone in the ovaries. Together with FSH, it stimulates the release of estrogen from Graafian follicles. It also induces the process of ovulation in which the mature ovum is extruded from the follicle and, following this, the cells which hitherto surrounded it are converted under the influence of LH into lutein cells (corpus luteum). In the male, it stimulates the interstitial cells of testes to secrete testosterone.

Kentsin is a tetrapeptide hormone (Thr-Pro-Arg-Lys) with contracentive properties.

LHRH is a neurohumoral hormone produced in the hypothalamus which stimulates the secretion of the pituitary hormones. LH and FSH (follicle-stimulating hormone), which in turn produce changes resulting in the induction of ovulation. Its amino acid sequence is pyroGlu-His-Trp-Ser-Tyr-Gly-Leu-Arg-Pro-GlyNH$_2$.

Neurotensin is a 13-residue-long peptide hormone exhibiting activities, e.g., hypertension, hyperglycemia, gut concentration, increased vascular permeability, enhanced secretion of ogrwoth hormone and hypothermic activity.

Substance P is an undecopeptide belonging to a group of proteins named tachykinins characterized by contractile action on extravascular smooth muscle. It also acts as a vasodilator, depressant, and like bradykinin, as a pain-producing agent. It stimulates salivation and produces increased capillary permeability. Its amino acid sequence is Arg-Pro-Lys-Pro-Gln-Phe-Phe-Gly-Leu-Met-NH$_2$.

Histones are small protein possessing a rather open, unfolded structure attached to DNA of cell nuclei by conic linkages. The are not hormones but are used as controls in tests associated with the present application.

The entry of $Ca^{2+}$ and/or $Mg^{2+}$ in many excitable cells can be inhibited by the calcium-channel antagonists (or blockers) which are drugs of major therapeutic importance. These drugs represent quite diverse classes of organic compounds. Verapamil, diltiazem and nifedipine are three main calcium-channel antagonists which have proven valuable in treating cardiac arrythmias and coronary disease. They bind strongly to the excitable cell membranes. A large number of synthetic analogues of these three major drugs have been made with the hope of improving their effectiveness. As is the case with the peptide hormones and their analogues, a common property of the calcium-channel antagonists (called "the drugs" hereinafter) and their analogues including agonists and synthetic commpounds, is their ability to bind $Ca^{2+}$ and/or $Mg^{2+}$, which is present in millimolar concentrations in the extracellular fluid. The $Ca^{2+}$- and/or $Mg^{2+}$- bound form is therefore the bioactive conformation of the drugs and their analogues.

Chemotaxis of polymorphonuclear leukocytes is the directed migration of these leukocytes along a chemical concentration gradient. Several small peptides are known to exhibit chemotactic behaviour towards leukocytes (i.e. neutrophils and eosinophils). The folded $\beta$-turn has been suggested as a conformation present in the free form of the naturally-occurring peptide chemoattractants. In addition to these, a large number of proteins, amino acids and synthetic peptides are chemotactic. One of the most active peptides is N-formyl methionyl-leucylphenylalanine (f-Met-Leu-Phe) and its derivatives.

These are only a few of the many naturally-occurring and synthetic agents, which effect a variety of physiological actions in the human body. It would therefore be desirable to provide a procedure and the means whereby the physiological effects of such naturally-occurring and synthetic agents may be mediated for the beneficial physiological effect it may have on the human body.

(b) Description of the Prior Art

U.S. Pat. No. 4,348,387 patented Sep. 7, 1982 by M. Brownlee et al provided a process and system for controlled delivery of a biologically active substance to an animal body fluid. The invention involved contacting fluid with a reversible complex of a conjugatae (1) and a binding macromolecule (2). The conjugate was a biologically-active portion which was intended to be proportionately released into a body fluid stream in response to varying concentration levels of a component of the body fluid stream, and a complexing substrate portion which conjugated with the biologically-active portion and which had affinity to the binding macromoleucle (2), competitively or non-competitively with the variable component of the body fluid. The component present in the body fluid was thus caused to complex to the binding macromolecule and thus to release the conjugate (1) therefrom into the fluid.

U.S. Pat. No. 4,392,996 patented Jul. 12, 1983 by L. A. Sternberger provided biologically-active peptide analogues by mixing a known biologically-active peptide with an affinity medium and separating the unknown peptide analogue by such techniques as liquid chromatography or electrophoresis. These biologically-active peptide analogues were found to react with receptors and thus to act as hormones which were said to have a more discriminating and longer lasting hormonal action than the original peptide.

U.S. Pat. No. 4,618,598 patented Oct. 21, 1986 by P. M. Conn provided a synthetic hormone complex having structure for binding to the surface of a cell and structure for altering second messenger mobilization by the cell. One form of the synthetic hormone complex functioned as an antagonist with specific binding affinity for a cell receptor of that hormone in combination with a calcium ion channel inhibitor. Another synthetic hormone complex functioned as an agonist comprising two or more molecules of a hormone having specific binding affinity for a cell receptor.

U.S. Pat. No. 4,668,772 patented May 26, 1987 by E. C. Lee provided a method for controlling the viscosity of protein hydrolysates by adjusting their magnesium and calcium content e.g. by reducing their viscosity by adding pyrophosphate or other precipitating agent to the hydrolysate and then removing the magnesium and-/or calcium precipitate that was formed thereby. Alternatively, the viscosity may be increased by adding a magnesium- and/or calcium-containing source.

U.S. Pat. No. 4,680,283 patented Jul. 14, 1987 by D. F. Veber, provided analogues of substance P and eledoisin which were conformationally constrained by the presence of a lactam in the peptide chain. Such analogues were said to demonstrate greater analgesic, anti-inflammatory, antihypertensive, central nervous system agents, and stimulants of lachrymal secretion.

U.S. Pat. No. 4,701,521 patented Oct. 20, 1987 by H. J. Ryser et al provided a method of effecting cellular uptake of molecules which were either excluded from cells or poorly transported into cells, such molecules being covalently bonded to a cationic polymer which served as a transport carrier to transport the molecules into cells.

SUMMARY OF THE INVENTION (a) Statements of Invention

It has been found that a major mechanism by which the physiological effects of the above-described and many other substances acting as stimuli are mediated involves the alteration in the intracellular concentration of free $Ca^{2+}$ ion. Thus, it has been found that: a) peptide hormones belonging to several classes; b) chemotactic peptides; c) drugs; and d) the synthetic analogues of these substances; are capable of binding $Ca^{2+}$ and/or $Mg^{2+}$ in nonpolar media with definite stoichiometries and, as such, are capable of transporting the $Ca^{2+}$ ion and/or $Mg^{2+}$ ion across synthetic lipid bilayer vesicles. The bioactive conformations of the natural or synthetic chemotactic peptides, proteins or other substances, are the respective $Ca^{2+}$-bound structures of these compounds.

Peptide hormones form a common link between the endocrine and nervous systems. Thus, hormones, e.g. insulin, glucagon, angiotensin II and members of the gastrin-cholecystokinin group are found in the brain where they may act as neurotransmitters. Peptide hormones belonging to different classes share the common property of binding to $Ca^{2+}$ and carrying this physiologically important cation into the lipid membrane. The requirement for $Ca^{2+}$ in the interaction of a hormone with its receptor has been highlighted in specific cases, e.g., insulin and ACTH. It has been found that the requirement for $Ca^{2+}$ and/or $Mg^{2+}$ in hormone-receptor interactions is general and arises in the form of the $Ca^{2+}$- and/or $Mg^{2+}$-bound structure of the hormone that is recognized by the receptor.

By this invention, novel mediating agents are provided herein, namely bioactive conformations of peptide hormones, neurotransmitters, calcium-channel antagonist drugs or chemotactic peptides, or analogues of all these compounds (including agonists, antagonists or synthetic analogues) having $Ca^{2+}$ and/or $Mg^{2+}$ ions optimally and optimally-conformationally bound to the respective compound.

The present invention also provides, as improved compositions of matter, bioactive conformations of peptide hormones, neurotransmitters, calcium-channel antagonist drugs or chemotactic peptides, or analogues of all these compounds angonists, or antagonists thereof or synthetic substances, having $Ca^{2+}$ and/or $Mg^{2+}$ ions conformationally bound to the respective compound, the composition comprising the combination of such compounds conformationally bound with $Ca^{2+}$ and/or $Mg^{2+}$ ions in a non-polar medium.

The present invention also provides a method for delivering $Ca^{2+}$ and/or $Mg^{2+}$ to a membrane-bound hormone receptor, comprising: transmitting $Ca^{2+}$ and/or $Mg^{2+}$ through a cell membrane using bioactive conformations of peptide hormones, neurotransmitters, calcium- and/or magnesium- channel antagonist drugs or chemotactic peptides, analgoues, agonists, or antagonists thereof or synthetic analogues thereof, having $Ca^{2+}$ and/or $Mg^{2+}$ ions conformationally bound to the respective compound.

The present invention also provides a method for mediating the physiological effects of peptide hormones, neurotransmitters, calcium-channel antagonist drugs or chemotactic peptides, analogues, agonists or antagonists thereof or synthetic analogues thereof having $Ca^{2+}$ and/or $Mg^{2+}$ ions conformationally bound to the respective compound, which method comprises: raising the concentration of intracellular $Ca^{2+}$ and/or $Mg^{2+}$ ions with a bioactive conformation of such peptide hormones, neurotransmitters, calcium-channel antagonist drugs or chemotactic peptides, analogues, agonists, or antagonists thereof or synthetic analogues thereof having $Ca^{2+}$ and/or $Mg^{2+}$ ions conformationally bound to the respective compound.

(b) Further Features of the Invention

In the novel mediating agents of this invention, the bioactive conformation may be of a peptide hormone or an analogue, agonist or antagonist thereof, or a synthetic analogue thereof, having $Ca^{2+}$ and/or $Mg^{2+}$ ions conformationally bound thereto, e.g. a peptide hormone which is selected from the group consisting of adrenocorticotropin hormone, angiotensin, vasopressin, oxytocin, bombesin, bradykinin, cholecystokinin, met-enkephalin, leu-enkephalin, endorphins, gastrins, glucogon, insulin, kentsin leutinizing hormone, follicle-stimulating hormone, LHRH, neurotensin, and tachykinins.

The bioactive conformation may be of a calcium-channel antagonist drug, agonist or antagonists thereof, or a synthetic analogue thereof, having $Ca^{2+}$ ions and/or $Mg^{2+}$ ions conformationally bound thereto, e.g. a calcium-channel drug which is selected from the group consisting of verapamil, diltiazem and nifedipine.

The bioactive conformation may be of a chemotactic peptide, its analogue, agonist or antagonist, or its synthetic analogue, having $Ca^{2+}$ ions and/or $Mg^{2+}$ ions conformationally bound thereto, e.g. a chemotactic peptide which is selected from the group consisting of f-met-leu-phe and f-met-norleucyl-phe.

In the novel compositions of matter, examples of non-polar media include alcohols, ketones e.g. methanol, ethanol, or propanol, e.g. acetone; ethers, e.g. dialkyl ether, and dioxane; and a variety of lipids, e.g. dimyristoyl phosphatidyl choline (DMPC), dipalmitoyl phosphatidyl choline, egg-lecithin, cholesterol, or diacylglycerol.

The bioactive conformation may be selected from any of the sub-groups as specially described in detail above.

In the method of the invention for delivering $Ca^{2+}$ and/or $Mg^{2+}$ to a membrane-bound hormone receptor, the bioactive conformation may be selected from any one of the sub-groups as specially described in detail above.

In the method of the invention for mediating the physiological effects of peptide hormones, the bioactive conformation may be selected from any one of the sub-groups as specifically described in detail above.

In all of the above methods and compositions of matter, $Mg^{2+}$ ions, when present, would compete with $Ca^{2+}$ ions for binding to the respective bioactive substance. The present invention therefore also include $Mg^{2+}$ ions in conjunction with, or in the place of, $Ca^{2+}$ ions.

BRIEF DESCRIPTION OF THE DRAWINGS

In the accompanying drawings.

DESCRIPTION OF PREFERRED EMBODIMENTS

The following experiments and examples are given to illustrate embodiments of the present invention.

EXAMPLE 1

Calcium transport across synthetic unilamellar lipid vesicles (ULV's) made from dimyristoylphosphatidylcholine (DMPC) by 0.1 mM glucagon at 17° C., the concentration of DMOC being 5 mM was carried out. The process was followed by monitoring the difference spectra due to $Ca^{2+}$ - Arsenazo III complex at different time intervals. The ULV's were prepared by sonication of multilamellar vesicles of the lipid in 5 mM $CaCl_2$, 0.145M MOPS at pH 7.4 and were maintained at 4° C. After removal of the external $Ca^{2+}$ by passage through a CHELEX-100 column, the vesicles were filtered through a 0.45 µm Millipore filter and treated with Arsenazo III (5 µM). 20 µl of a 5 mM hormone solution in water or methanol was added to 1 ml of the solution in the sample cuvette and 20 µl of the buffer was added to the reference cuvette solution and stirred. The total trapped $Ca^{2+}$ concentration was estimated by adding 0.1 ml of a 1% TRITON solution to the sample or reference solution. This solution was analysed for $Ca^{2+}$ transport by use of a Difference Spectroscopic method.

Figure 1:
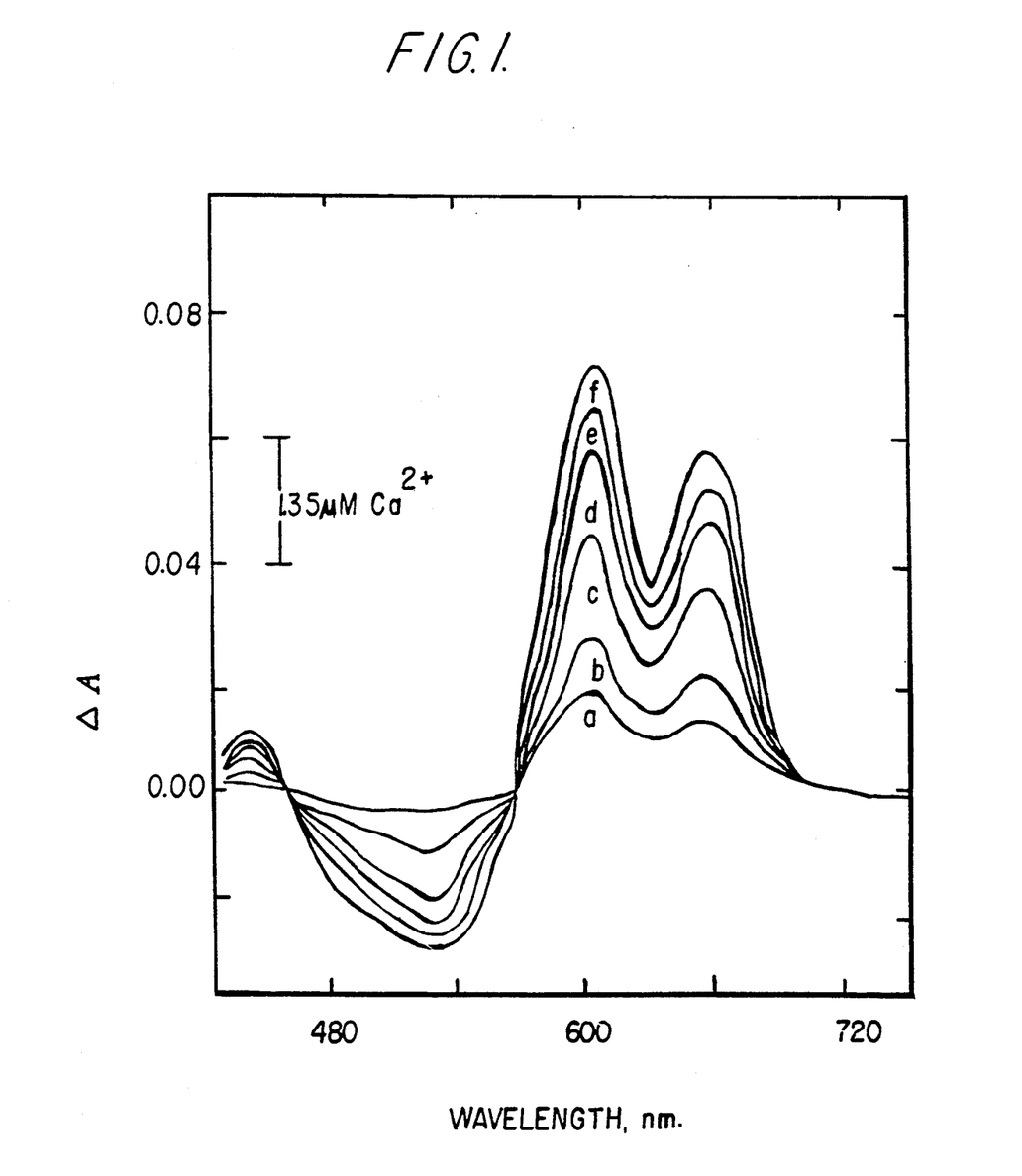
FIG. 1 is a graph showing the translocation of $Ca^{2+}$ across unilamellar vesicles (ULV's) of DMPC by glucagon.

The results are summarized in FIG. 1. FIG. 1 shows the data obtained with glucagon at 17° C. at a pH of 7.4, using a lipid concentration of 5 mM and a lipid:peptide ratio of 50. Shown are spectra at: a, 7 minutes; b, 21 minutes; c, 80 minutes; d, 140 minutes; e, 200 minutes and f: 260 minutes. The $Ca^{2+}$ trapped inside the vesicles is released progressively with time as seen from the increase in the magnitudes of the difference absorption at the peaks at 595 and 656 nm. These changes were not measurable at 15° C., too fast to measure at 22°–24° C. (the gel-liquid crystalline transition temperature of DMPC) and moderately fast at 45° C. The $Ca^{2+}$ transport is therefore of the carrier type.

Experiments with the synthetic peptide tBoc-Leu-Pro-Tyr-Ala-$NHCH_3$ showed that the cation transport was of the carrier and not the channel type and analysis of the kinetic data obtained at different peptide concentrations showed the transporting species to be a 2:1 peptide $Ca^{2+}$ sandwich complex. Using a similar experimental protocol, the $Ca^{2+}$ transport abilities of glucagon, substance P, Leu-enkephalin, Met-enkephalin, D-$Met^2$, $Pro^5$-ehkephalin, α-endorphin, adrenocorticotropin, residues 1-10 [ACTH (1-10)] and leutinizing hormone releasing hormone (LHRH) were examined.

Similar data were obtained with substance P, Met-enkephalin and its D-$Met^2$-$Pro^5$ derivative, α-endorphin, ACTH (1-10) and LHRH (data not shown). For the same molar concentration of the peptide, the $Ca^{2+}$ transport was found to be extremely slow with Leu-enkephalin when compared with the Met counterparts, although the transport by the former peptide could still be detected with respect to the reference containing no peptide. With insulin and bradykinin, although the spectral changes observed were still as dramatic as with glucagon, the spectral maxima were shifted.

EXAMPLE 2

The ability of the peptide hormones to transport the $Ca^{2+}$ analog, $Pr^{3+}$, was investigated by the use of Nuclear Magnetic Resonance (NMR) method. This makes use of the paramagnetic shift, caused by $Pr^{3+}$, of the relatively sharp NMR signals of the choline methyl protons of the lipid in the liquid crystalline phase. The ULV's were made in $D_2O$ containing 0.145M KCl-NaCl having a nominal pH of about 7.0. $Pr(NO_3)_3$ in $D_2O$ was then added to a concentration of 10 mM. The movement of the $N(CH_3)_3$ proton resonance of the choline head groups in the vesicle interior towards that of the outer head groups was monitored as a function of time.

Figure 2:
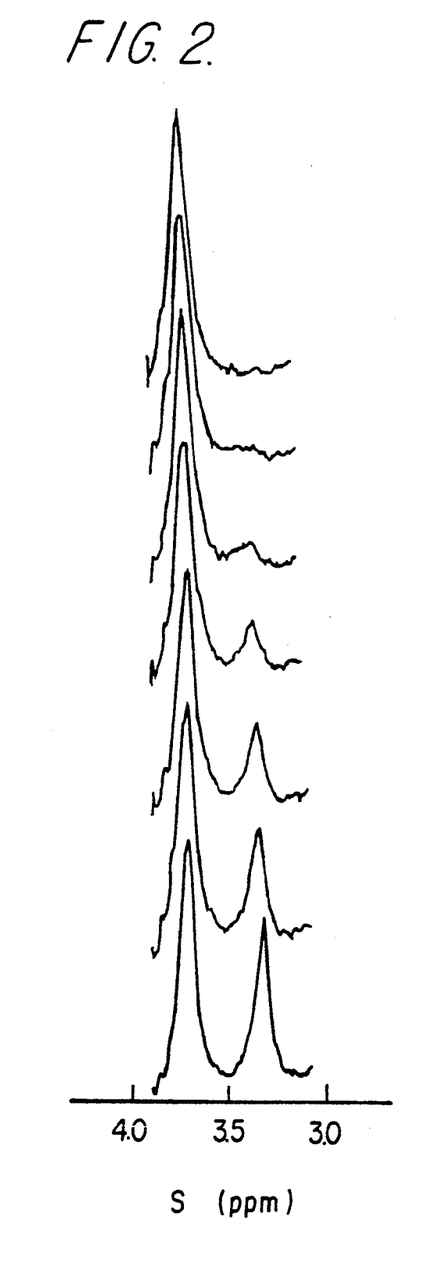
FIG. 2 is a graph showing the translocation of $Pr^{3+}$ across unilamellar vesicles (ULV's) of DMPC by glucagon.

FIG. 2 shows spectra at 5 minutes time intervals, starting with 0 time at the bottom. With $Pr^{3+}$ initially present in the buffer outside the vesicles, one observes the movement of the peak due to the inner methyl protons towards that of the outer methyl protons as $Pr^{3+}$ is translocated by a peptide carrier. The results obtained with glucagon (75 µM in 15 mM lipid, lipid:peptide ratio 200), at 45° C. and pH 7.4, are shown in FIG. 2. The rate of transport of the cation was found to be too fast to measure at a lipid:glucagon ratio of 25 and too slow at a ratio of 800. No transport was detected at 12° C. where the lipid exists in the gel state.

Similar data were obtained with insulin which exhibited a higher rate of $Pr^{3+}$ transport than glucagon, the transport being measurable even at a lipid:peptide ratio of 1000 (insulin concentration 15 µM). Bradykinin and substance P showed a measurable rate only at much higher peptide concentrations (lipid:peptide ratio of 25). $Pr^{3+}$ transport by the other peptide hormones were not measurable even at higher peptide concentrations. This may reflect the inability of these peptides to bind and/or transport $Pr^{3+}$ in contrast to their behaviour towards $Ca^{2+}$. Control experiments with the synthetic peptides tBoc-Gly-Pro-Pro-OH and H-$(Pro)_4$-OH and with histone showed no transport of either $Ca^{2+}$ or $Pr^{3+}$ over the periods of measurement used for the test peptides.

EXAMPLE 3

In order to determine whether peptide hormones would bind $Ca^{2+}$, solution of substance P, bradykinin, LHRH, ACTH (1-10) and, to a limited extent, angiotensin II and bombesin, were titrated with $Ca(ClO_4)_2$ in acetonitrile or acetonitrile, methanol solvent mixture and the changes in the CD spectra of the peptides were monitored.

Figure 3:
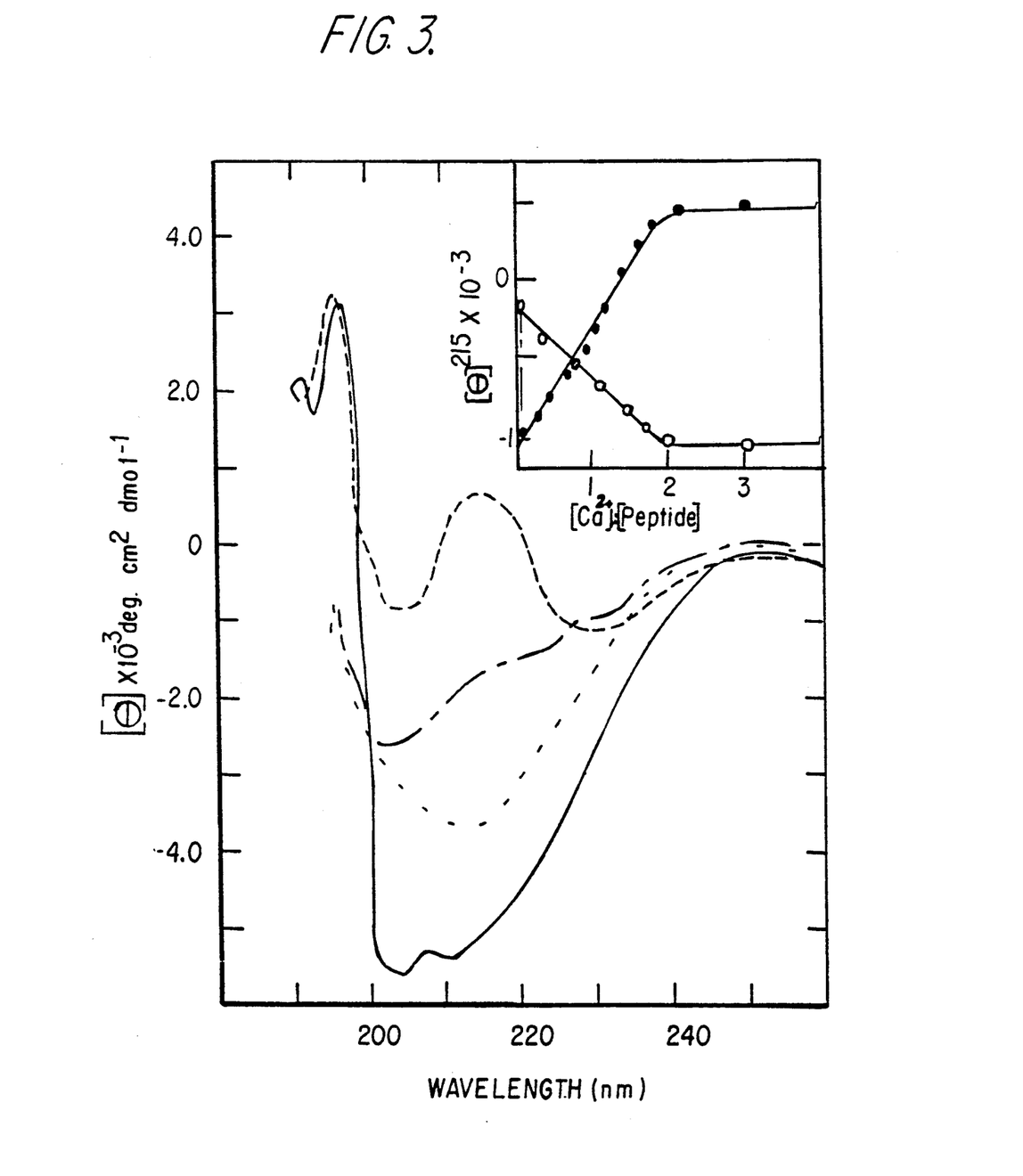
FIG. 3 is a graph showing the effect of $Ca^{2+}$ in the CD spectra of substance P and bradykinin.

The data obtained (shown in FIG. 3 for substance P and bradykinin) indicate that these peptides bind $Ca^{2+}$ with definite stoichiometries. The CD spectral data indicate that the conformation of the $Ca^{2+}$-bound form of the hormone is quite different from that of the free hormone in the non-polar environment.

EXAMPLE 4

Experiments have been conducted to show the effect of $Ca^{2+}$ inhibition by calcium-channel antagonists. These experiments to illustrate these embodiments of the present invention are identical to those described for peptide hormones and they demonstrate that verapamil, nifedipine and diltiazem and their analogues bind $Ca^{2+}$ stoichiometrically in a nonpolar environment and transport this cation across lipid bilayer membrane. In addition, the difference absorption spectrum between the particular drug and its $Ca^{2+}$-bound form has been used as a tool to demonstrate $Ca^{2+}$ binding by the drug.

EXAMPLE 5

The bioactive conformation of the natural and synthetic chemotactic peptides and protein have been demonstrated by showing that representatives of chemotactic peptides, e.g., f-met-leu-phe and f-met-norleucyl-phe bind $Ca^{2+}$ in a nonpolar medium (e.g. as would exist in a lipid-bound membrane receptor) can transport $Ca^{2+}$ across the lipid membrane. The protocols for these experiments are similar to those described for peptide hormones.

USE OF THE INVENTION

In respect of the binding of $Ca^{2+}$ by linear synthetic peptide, it has been found that while the cation is held in the polar 'interior' (formed of carbonyl and/or carboxylic ligands) of the peptide, the peptide exterior is relatively non-polar (formed of sidechain groups). Thus, the $Ca^{2+}$-bound conformation of the peptide would induce (or enhance) the amphiphilic structure and, as such, would facilitate both the interaction of the peptide with and the carriage of the cation through the non-polar lipid bilayer. This appears to be the case with the peptide hormones in the model lipid bilayer system.

To the extent that the data show that the hormone-$Ca^{2+}$ complex can move freely through a membrane, they can be taken to indicate that the interaction of this complex with a membrane-bound receptor is feasible in or near the membrane-spanning segment(s) of the receptor. It is believed that the receptors may themselves have $Ca^{2+}$-binding sites in them. Thus, the transport of $Ca^{2+}$ by the hormone through the membrane might be a mechanism to "deliver" the cation to the membrane-bound receptor. One may visualize a ternary complex of the receptor-hormone-$Ca^{2+}$ as an intermediate in the formation of a conformationally-altered receptor which would release the $Ca^{2+}$ within the membrane (along with the dissociated hormone). This, in turn, may trigger several subsequent $Ca^{2+}$-dependent processes, e.g. the autophosphorylation of the receptor, and the actions of phospholipase C and protein kinase C. $Ca^{2+}$ influx caused by the direct transport of $Ca^{2+}$ through the lipid bilayer by the hormone (as found in the case of the $Ca^{2+}$ ionophore A23187) is possible. This mechanism is unlikely in the presence of the interacting receptor which could subsequently operate the $Ca^{2+}$ channels in the membrane.

The $\beta$-turn has been implicated as a common structural feature in many peptide hormones. In view of the above disclosure relating to linear $\beta$-turn model peptides, it has been found that several peptide hormones can selectively bind $Ca^{2+}$ in non-polar solvents. Many of these peptides can transport $Pr^{3+}$ and $Ca^{2+}$ ions across synthetic unilamellar lipid vesicles (ULV's). Some of them mimic the action of the calcium ionophore A23187 in affecting the activity of sarcopoasmic $Ca^{2+}$-$Mg^{2+}$ ATPase. (data not shown) They also increase the intracellular free $Ca^{2+}$ in fibroblast cell cultures (data not shown). These effects of the peptide hormones are presently accounted for by their $Ca^{2+}$ binding and translocating properties.

It has been found that the hormone-receptor interaction takes place in the presence of millimolar concentrations of extracellular $Ca^{2+}$. Since the binding constants for the peptide hormone $Ca^{2+}$ complex range between $10^3$ to $10^4 M^{-1}$, this complex will be present in the physiological range of concentrations of the peptide hormones themselves. Hence it is proposed that the bioaxtive conformation of the peptide hormone corresponds to that of the $Ca^{2+}$-bound form. This conformation would be stabilized in the non-polar lipid bilayer. This information should be useful in designing analogs of the peptide hormones as well as their agonists and antagonists.

The connecting link of similarities among the peptide hormones has been found to be their $Ca^{2+}$-binding property. Several peptide hormones have been found to bind calmodulin. The binding is $Ca^{2+}$-dependent and may be viewed, analogous to the hormone-receptor interaction, as an interaction where both the participating molecules bind the cation; the insulin receptor has, in fact, a calmodulin binding site which is believed t be proximal to its $Ca^{2+}$- and insulin-binding sites. Several peptide hormones, including glucagon and insulin, are known to inhibit the activities of membrane-bound $Ca^{2+}$-$Mg^{2+}$ ATPases, a property exhibited also by the calcium ionophore A23187. The present disclosure of experiments using depletion of extracellular $Ca^{2+}$ have indicated the involvement of this ion in mediating the effects of insulin, ACTH, LHRH and angiotensin II; the last peptide has, in fact, been shown to translocate $Mn^{2+}$ ion across synthetic lipid vesicles. Neuropeptide receptor agonists, such as substance P, neurotensin, bradykinin, somatostatin, vasoactive intestinal polypeptide and dynorphin mimic A23187 and induce a receptor-independent histamine release from mast cells which apparently involves their calcium-transporting property.

It is believed that the calcium-binding region of a peptide hormone can be considered to be involved in the transduction part, while another region of the hormone (particularly that containing Arg and Lys residues) may enhance the binding of the peptide to the receptor. This is analogous to substrate-enzyme enteraction involving binding and catalytic site. The action of agonists of a given peptide hormone as well as the "cross-reactivity" found among peptides, such as insulin and the insulin-like growth factors and oxytocin, may arise from similarities in their calcium-bound conformations which would elicit the transduction response from the receptor.

CONCLUSION

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What we claim is:

1. A pharmaceutical composition comprising (a) a compound selected from the group consisting of peptide hormones, neuro-transmitters, calcium channel antagonists, chemotactic peptides, and their agonists, antagonists and analogues, (b) a source of $Ca^{++}$ or $Mg^{++}$ ions, and (c) a solvent selected from the group consisting of alcohols, ketones, ethers and lipids, wherein said mediating agent binds to said $Ca^{++}$ or $Mg^{++}$ ion and, as a result of such binding, assumes a bioactive, amphiphilic conformation which is different from the conformation of said mediating agent in said solvent prior to binding.

2. The composition of claim 1 in which the compound is a peptide hormone.

3. The composition of claim 1 in which the compound is a calcium channel antagonist.

4. The composition as claimed in claim 3 wherein said calcium-channel antagonist is selected from the group consisting of verapamil, diltiazem and nifedipine.

5. The composition of claim 1 in which the compound is a chemotactic peptide.

6. The composition of claim 1 in which the solvent is a lipid.

7. The composition of claim 6 wherein said solvent is dimyristoyl phosphatidyl choline.

8. The composition as claimed in claim 2 wherein said peptide hormone is selected from the group consisting of adrenocorticotropin hormone, angiotensin, vasopressin, oxytocin, bombesin, bradykinin, cholecystokinin, met-enkaphalin, leu-enkaphalin, endorphins, gastrins, glucogen, insulin, kentsin leutinizing hormone, follicle-stimulating hormone, LHRH, neurotensin, and tachykinins.

* * * * *